United States Patent
Chandler et al.

(10) Patent No.: US 7,607,824 B2
(45) Date of Patent: Oct. 27, 2009

(54) METHOD OF ANALYZING ELECTRICAL CONNECTION AND TEST SYSTEM

(75) Inventors: Brian Lee Chandler, Kokomo, IN (US); Frederick F. Kuhlman, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 223 days.

(21) Appl. No.: 11/586,456

(22) Filed: Oct. 25, 2006

(65) Prior Publication Data

US 2008/0101435 A1 May 1, 2008

(51) Int. Cl.
G01N 25/20 (2006.01)
G01K 1/16 (2006.01)

(52) U.S. Cl. ............................ 374/5; 374/44; 374/57; 374/120; 374/137; 702/34; 382/145; 250/338.1

(58) Field of Classification Search ............. 374/43–45, 374/57, 4, 5, 29, 112, 137, 121, 124, 135, 374/30, 100, 115, 166, 167, 129, 183; 324/760, 324/65; 382/145–147, 149–150; 250/341.1–341.2, 250/341.4, 341.6, 341.8, 340; 702/34–36
See application file for complete search history.

(56) References Cited

U.S. PATENT DOCUMENTS

| | | | | |
|---|---|---|---|---|
| 4,999,499 A | * | 3/1991 | Bhatt | 250/342 |
| 5,246,291 A | * | 9/1993 | Lebeau et al. | 374/5 |
| 5,717,248 A | * | 2/1998 | Neumann et al. | 257/718 |
| 6,428,202 B1 | * | 8/2002 | Mitsuhashi et al. | 374/5 |
| 6,489,780 B2 | * | 12/2002 | Yoshida | 324/538 |
| 6,765,396 B2 | * | 7/2004 | Barror | 324/753 |
| 6,971,791 B2 | * | 12/2005 | Borden et al. | 374/5 |
| 7,324,685 B2 | * | 1/2008 | Mejias Miranda | 382/147 |
| 2006/0046550 A1 | * | 3/2006 | Lalonde | 439/268 |
| 2006/0193038 A1 | * | 8/2006 | Regan et al. | 359/402 |
| 2007/0010139 A1 | * | 1/2007 | Chen | 439/751 |
| 2007/0144182 A1 | * | 6/2007 | Sauciuc et al. | 62/3.2 |
| 2008/0003892 A1 | * | 1/2008 | Fassel et al. | 439/751 |
| 2008/0033664 A1 | * | 2/2008 | Yamanoto et al. | 702/36 |
| 2008/0102663 A1 | * | 5/2008 | Sakai | 439/108 |

FOREIGN PATENT DOCUMENTS

JP 60243574 A * 12/1985
JP 2001280935 A * 10/2001

OTHER PUBLICATIONS

"Beat the Heat" by John Pratten III, published in EC&M at http://ecmweb.com/mag/electric_beat_heat/ on Aug. 1, 2006, 5 pages.

* cited by examiner

*Primary Examiner*—Gail Verbitsky
(74) *Attorney, Agent, or Firm*—Jimmy L. Funke (57) ABSTRACT

A test system and method of analyzing a pin to circuit connection on a substrate is provided. The method includes applying thermal energy to the pin or the substrate at a location outside of the pin to circuit interface, and measuring infrared radiation near the pin to circuit interface. The method also includes the step of analyzing the measured infrared radiation to determine thermal energy distribution near the pin to circuit interface resulting from thermal conductivity at the interface. The method further includes the step of determining sufficiency of the pin to circuit electrical and mechanical connection based on the determined thermal energy distribution.

25 Claims, 6 Drawing Sheets

METHOD OF ANALYZING ELECTRICAL CONNECTION AND TEST SYSTEM

TECHNICAL FIELD

The present invention generally relates to quality inspection of electrical connections and, more particularly, relates to a method of analyzing electrical connection of pin(s) to circuitry on a substrate to ensure an adequate quality electrical and mechanical connection.

BACKGROUND OF THE INVENTION

Compliant pin electrical connections typically employ electrically conductive pins forcibly press-fit inserted into conductive vias (e.g., plated through holes) to form electrical interconnections, in lieu of requiring solder joints. Compliant pin electrical connections offer advantages over traditional soldering processes due to the lack of heat exchange, enhanced speed in assembly, and the need for less expensive capital equipment. The compliant pin connections typically have no solder joints to inspect to determine the quality of the soldered connection. Instead, a quality concern of the conventional press-fit pin to conductive vias connectors is whether a plated through hole receptacle is too large or a press-fit pin is too small to make adequate electrical contact with the plated through hole.

One conventional press machine employed to assemble and insert compliant pins forcibly into plated through holes typically monitors the force and distance of the compliant pins as they are inserted into the holes in the substrate to make electrical and physical contact with the plated through hole. When a multiple pin part is assembled onto a circuit board, it is often difficult for the press machine to detect a pin or plated through hole that is slightly out of specified size due to variations in the assembly process. A non-destructive method of analyzing the press-fit connections is generally needed in the production environment to ensure high quality electrical connections are realized, especially for automotive applications.

In the past, electronics manufacturers and assemblers have employed destructive sampling techniques which involve cutting up sample circuit boards to examine the electrical and mechanical circuit connections for quality control purposes. Other conventional techniques have employed measuring the resistance across the pin to circuit connections on the circuit board. The conventional resistance measurement technique generally involves applying electrical current to each of the electrical contacts and measuring the electrical resistance. This conventional quality measurement process is generally time consuming. Additionally, it is generally difficult to connect test connectors to the multiplicity of pins, and often requires a special board layout to accommodate the testing procedure. Further, the conventional measurement process may not always detect a weak mechanical connection.

Accordingly, it is therefore desirable to provide for a technique of measuring electrical conductivity between one or more pins and circuitry on a substrate that cost-effectively determines the quality of the resulting electrical connections. Further, it is desirable to provide for such a testing method that is quick and easy to use and does not impose special requirements on the design configuration of the electrical circuitry.

SUMMARY OF THE INVENTION

In accordance with one aspect of the present invention, a method of analyzing a pin to electrical circuit connection on a substrate is provided. The method includes the step of applying thermal energy to one of the pin and the substrate at a location outside of the pin to circuit interface, and measuring thermal energy radiation near the pin to circuit interface. The method also includes the step of analyzing the measured thermal energy radiation to determine thermal energy distribution near the pin to circuit interface resulting from thermal conductivity of the interface. The method further includes the step of determining quality of the pin to circuit electrical connection based on the determined thermal energy distribution.

According to another aspect of the present invention, a test system is provided for determining quality of an electrical connection between a pin and a circuit on a substrate. The test system includes a heat source for applying thermal energy to one of a pin and the substrate at a location outside of the pin to circuit interface. The test system also includes a thermal energy measuring device for measuring thermal energy radiation near the pin to circuit interface. The test system further includes a processor for analyzing the measured thermal energy radiation to determine thermal energy distribution near the pin to circuit interface resulting from thermal conductivity at the interface. The processor further determines quality of the pin to circuit electrical connection based on the determined thermal energy distribution.

The method and test system advantageously results in a cost-effective test procedure that is quick and easy to employ. Specifically, the method and system applies thermal energy and measures thermal conductivity through the pin to circuit connection in a manner that is not intrusive to the circuit components to check the electrical and mechanical connection quality of the resulting electronic device.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
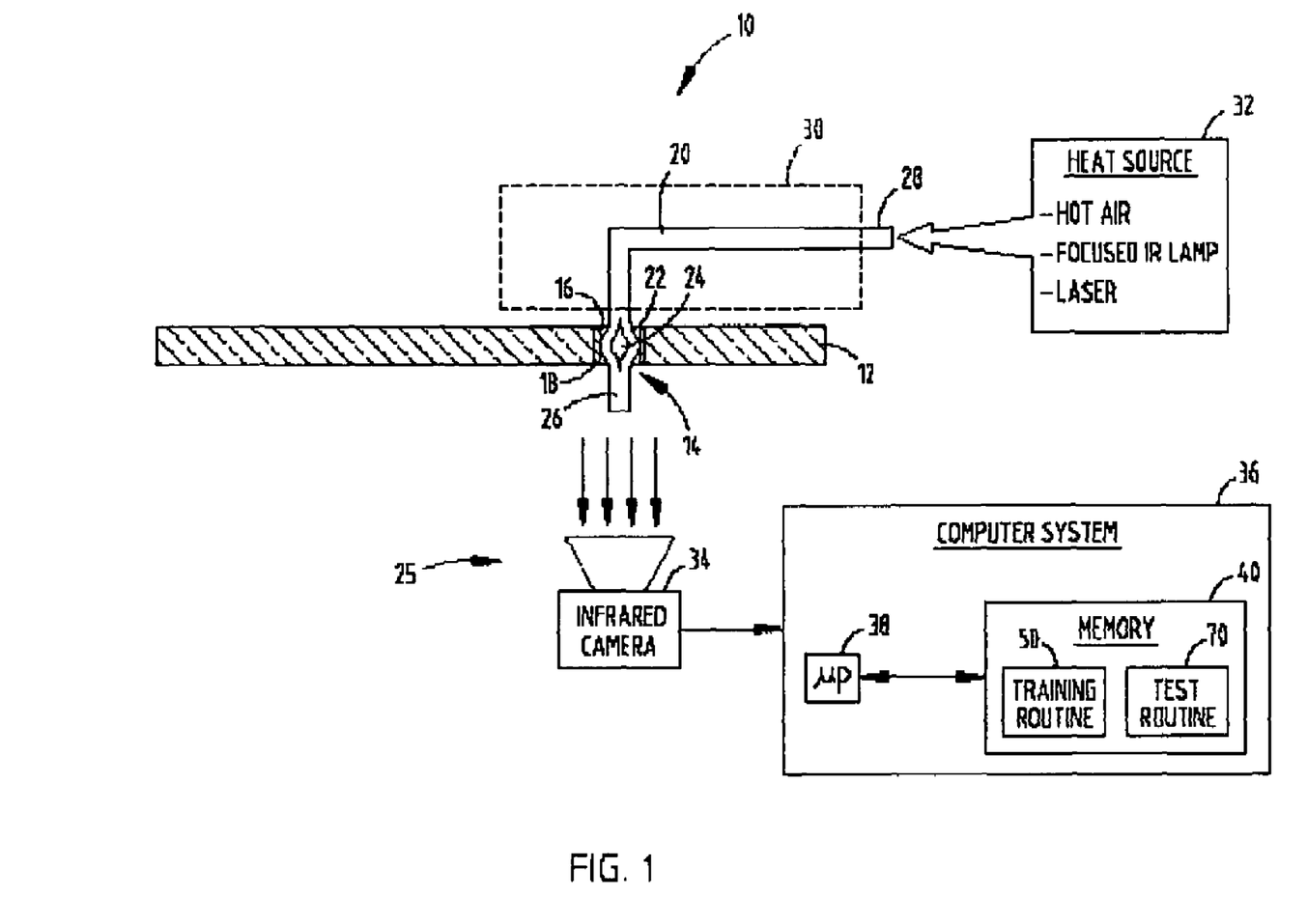
FIG. 1 is a schematic diagram illustrating a test system testing the pin to circuit connection on a substrate according to one embodiment of the present invention.

Referring to FIG. 1, an electronic package 10 is generally illustrated in relation to an electrical connection test system 25 for testing the electrical and mechanical connections on the package 10. The electronic package 10 generally includes a substrate 12, such as a printed circuit board, which includes electrical circuitry, such as circuit traces formed on or in a dielectric substrate material. The circuit board 12 also includes connecting circuitry in the form of one or more plated through holes 14 extending into or through the dielectric substrate 12. The plated through holes 14 generally include a hole 16, which may be formed by drilling or other known techniques, and an electrically conductive material 18 plating the opening 16. One example of electrically conductive material may include copper. The plated through hole 14 provides an electrical circuit connection through the substrate 12 as is known in the art. The substrate 12 may include any known substrate material such as FR4.

The electronic package 10 is further shown including a compliant conductive pin 20 having a bend in the shape of an L, according to an exemplary embodiment. In many typical packages, a plurality of conductive pins 20 may be present. The compliant conductive pin 20 is a press-fit electrical connector pin having an enlarged compliant portion 22 formed near one end 26 adapted to be press-fit into the plated through hole 14 of substrate 12. In the embodiment shown, the enlarged compliant portion 22 of pin 20 has side walls that bulge out and an inner hollow portion 24. As one end 26 of pin 20 is forcibly inserted into the plated through hole 14 of substrate 12, the enlarged compliant portion 22 is squeezed into the plated through hole 14 such that it is press-fit and compressed within the plated through hole 14 to form electrical contact with the electrically conductive plating 18. One or more compliant press-fit pins 20 of various shapes and sizes may be employed to engage connecting circuitry on the substrate 12 to form electrical connection(s) on an electronic package 10 to be tested by test system 25.

The compliant press-fit pin 20 is further shown located within a connector housing 30. It should be appreciated that any connector housing 30 may be employed to house one or more pins 30, such that the pins 30 are adapted to engage with circuitry on substrate 12. The pin 20 may also be connected to substrate 12 without a connector housing. Opposite end 26 of conductive pin 20 is end 28 which may further be connected to other circuitry to complete an electrical circuit path. It should be appreciated that a plurality of conductive pins 20 may be employed within a common connector housing 30 and each connected to circuitry on the substrate 12.

The electrical connection test system 25 is employed to test the electrical conductivity and mechanical connection between the conductive pin 20 and the circuitry 18 on substrate 12. The test system 25 as shown in the first embodiment of FIG. 1 employs a heat source 32 for applying thermal energy to one end 28 of conductive pin 20. The heat source 32 may include any source of thermal energy (e.g., electric heat lamp) that applies hot air via convection, according to one embodiment. According to another embodiment, the heat source 32 may include an infrared (IR) lamp focused onto the pin 20 for applying infrared thermal energy radiation to the conductive pin 20. According to a further embodiment, the heat source 32 may include a laser for applying thermal energy in the form of a laser beam to the conductive pin 20.

The test system 25 also includes an infrared camera 34 and a computer system 36 for monitoring the conductive heat transfer of thermal energy near the interface of the pin 20 and circuitry 18 on substrate 12. The infrared camera 34 may include any of a number of known infrared measuring devices for monitoring infrared radiation from a detection area. One example of an infrared camera 34 may include Model No. Merlin Midwave IR 9705, commercially available from Indigo Systems. The infrared camera 34 is located so as to detect infrared thermal energy radiation from a detection region near where the pin 20 interfaces with and connects to the plated through hole circuit 14 in substrate 12.

The computer system 36 included in the test system 25 according to the illustrated embodiments is shown having a microprocessor 38 and memory 40. Any microprocessor or other processor circuitry may be employed to analyze the captured infrared images and determine the sufficiency of the electrical connection based upon the sensed thermal energy radiation, according to the present invention. The memory 40 may include random access memory (RAM), read-only memory (ROM), electrically erasable programmable read-only memory (EEPROM), or other known volatile or non-volatile memory as should be evident to those skilled in the art. Stored within memory 40 is a training routine 50 and a test routine 70, as explained hereinafter. The computer system 36 generally processes the infrared thermal energy radiation captured by the infrared camera 34, compares the infrared radiation distribution to trained information, and executes the test routine 70 to determine if the electrical conductivity and mechanical connection between pin 20 and circuit 18 of substrate 12 is sufficient.

According to the first embodiment, the test system 25 applies thermal energy by way of heat source 32 to one end 28 of conductive pin 20. The thermal energy is conducted via conductive heat transfer through pin 20 such that it is transmitted to the plated through hole 14. If a suitable physical connection is present between the pin 20 and the circuit 18 at the plated through hole 14, the thermal energy is distributed by way of conductive heat transfer to the connecting circuit 18 and substrate 12. The infrared camera 34 captures the thermal energy from near the interface of the pin 20 and the circuit 18, preferably within a distance of about two millimeters from the interface. The computer system then monitors and evaluates the sensed thermal energy radiation to determine if a sufficient electrical and mechanical connection exists at the interface.

Figure 2:
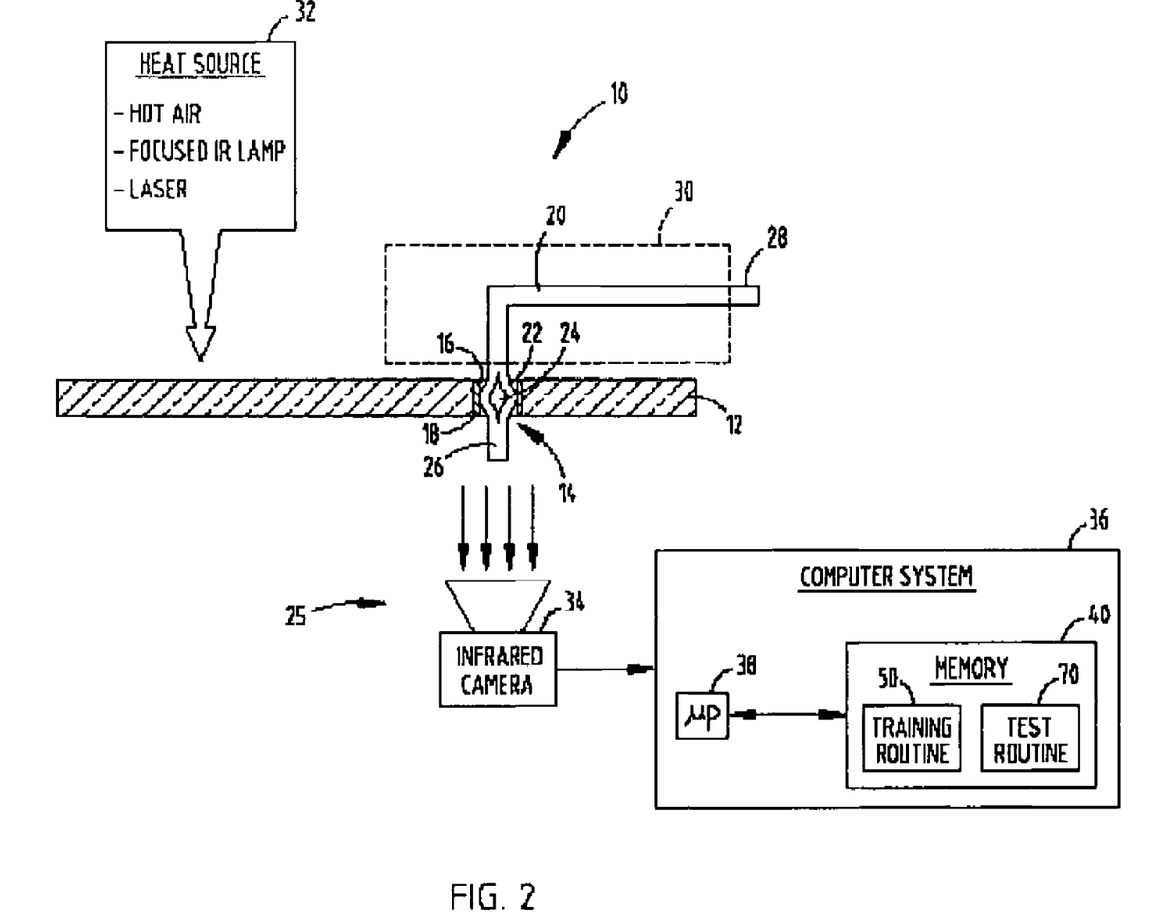
FIG. 2 is a schematic diagram illustrating a test system testing the pin to circuit connection on a substrate according to a second embodiment of the present invention.

Referring to FIG. 2, the test system 25 is shown according to a second embodiment. In the second embodiment, the heat source 32 is applied to the substrate 12 at a location outside the pin to circuit interface, instead of the one end 28 of conductive pin 20. By applying the heat source 32 to the substrate 12, thermal energy is applied to the substrate 12 which passes to the circuitry 28 of plated through hole 14 by way of conductive heat transfer and, provided a suitable physical connection is present between pin 20 and circuitry 18, thermal energy is conducted onto the pin 20 at the interface. The infrared camera 34 captures the thermal energy from near the interface of the pin 20 and circuit 18, particularly in the region where the pin 20 is located to measure the thermal energy transferred to the pin 20. The computer system 36 then monitors and evaluates the sensed thermal energy radiation to determine if a sufficient electrical and mechanical connection exists at the interface.

Figure 3:
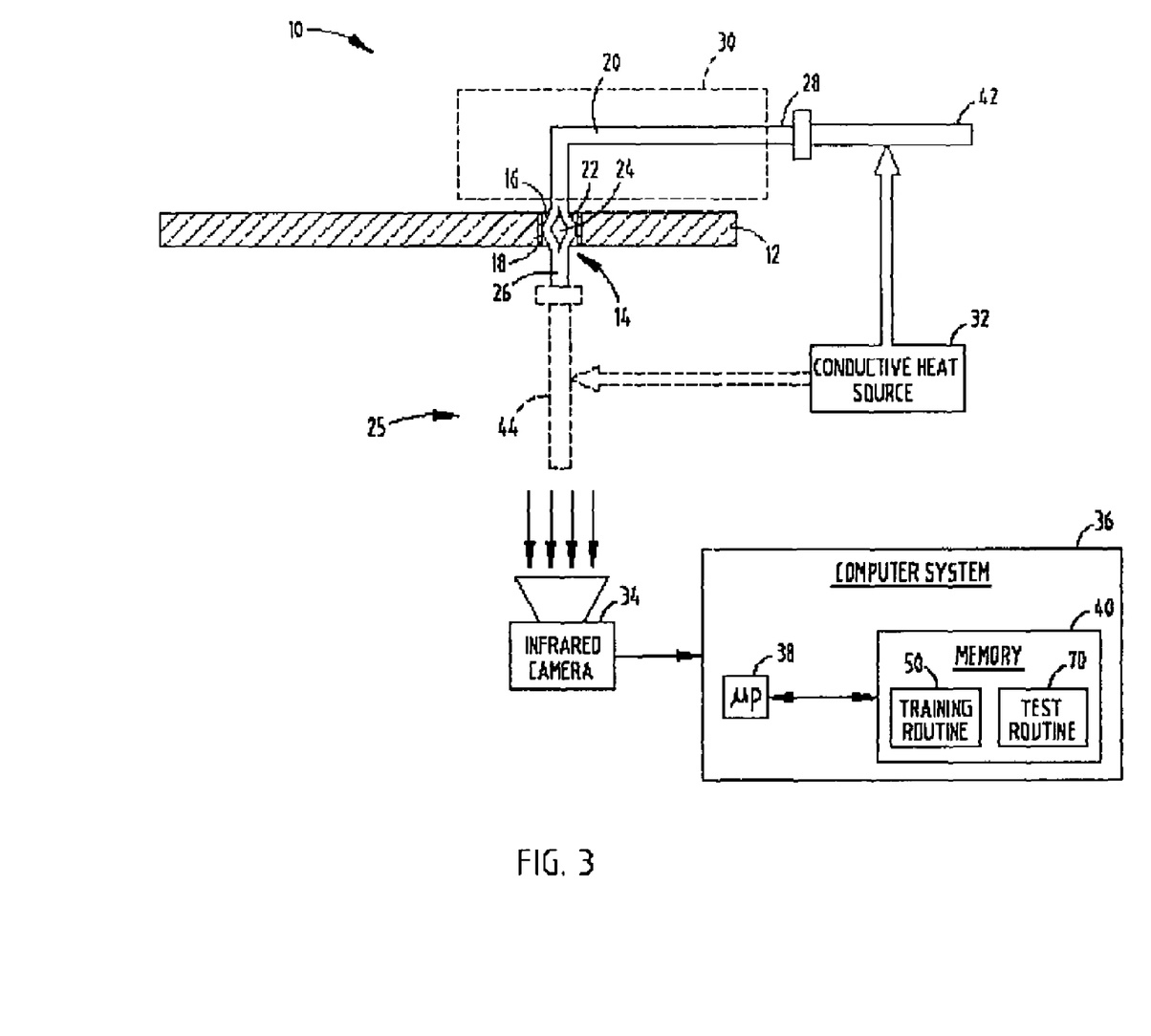
FIG. 3 is a schematic diagram illustrating a test system testing the pin to circuit connection on a substrate according to a third embodiment of the present invention.

Referring to FIG. 3, a test system 25 is illustrated according to a third embodiment for testing the electrical conductivity between the conductive pin 20 and circuit 18 of substrate 12. According to the third embodiment, the test system 25 employs a conductive heat source 32 connected to one of thermal conductive pins 42 and 44 that, in turn, are connected to respective opposite ends 28 and 26 of pin 20. The one of the conductive heat pins 42 or 44 transfers heat via conductive heat transfer to pin 20 so as to heat one end of pin 20. The thermal energy applied to one end of pin 20 is conductively transferred to the interface of the pin 20 and circuitry 18. The infrared camera 34 senses the infrared thermal energy near the pin to circuit interface, and the computer system 36 then monitors the sensed infrared radiation and evaluates whether or not a sufficient electrical and mechanical connection is present between the pin 20 and circuitry 18.

Figure 4:
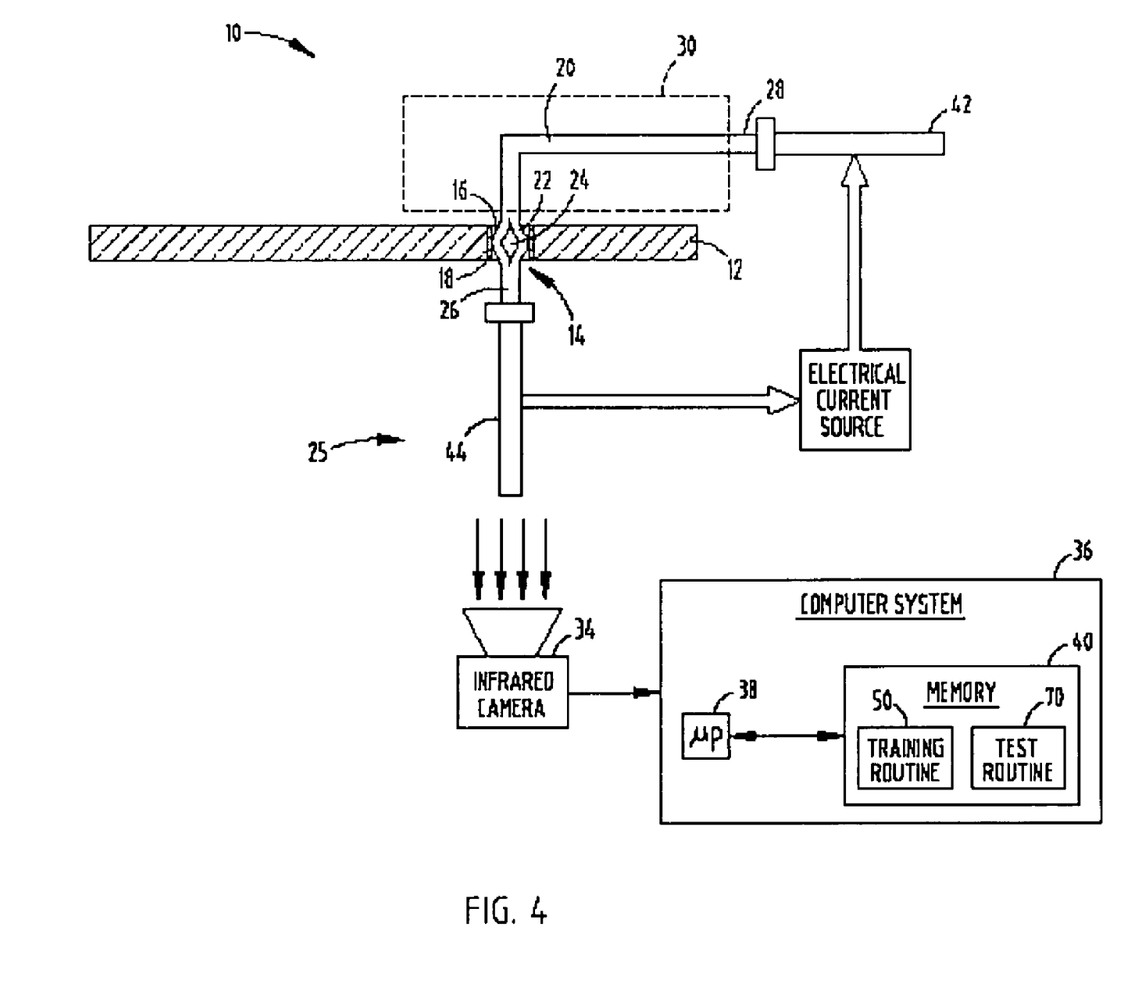
FIG. 4 is a schematic diagram illustrating a test system testing the pin to circuit connection on a substrate according to a fourth embodiment of the present invention.

Referring to FIG. 4, the test system 25 is further illustrated according to a fourth embodiment employing an electrical current source 46. According to the fourth embodiment, the electrical current source 46 supplies electrical current to one end of pin 20. This may be achieved by applying a voltage to either end 23 or 26 of pin 20 via pins 42 or 44. A return current path or a ground connection may be provided at the opposite end of pin 20 to provide a closed circuit arrangement. In doing so, the application of electrical voltage to one end of pin 20 causes the electrical current to flow on the pin 20 and, in the process, generates thermal energy in the pin 20 due to the resistance of the pin 20. The generated thermal energy in the pin 20 is then transferred via thermal conduction to the interface of the pin 20 and circuitry 18 and the surrounding substrate 12, provided a proper electrical connection is present. The test system 25 then evaluates the infrared radiation radiated near the interface of the pin 20 and circuit 18 to determine the sufficiency of the electrical and mechanical connection.

Figure 5:
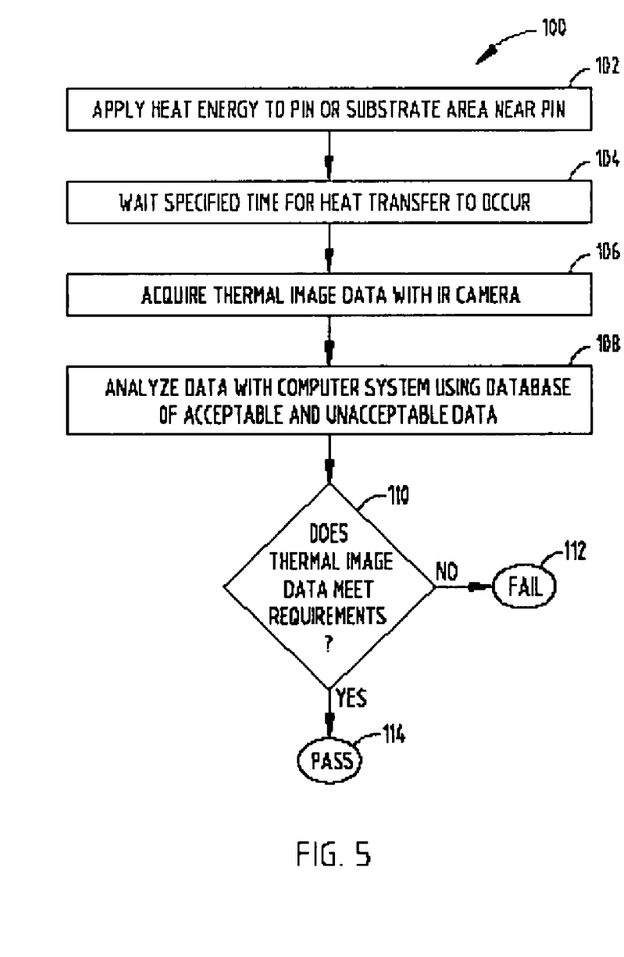
FIG. 5 is a flow diagram illustrating a test analysis method for determining quality of the electrical and mechanical connections according to one embodiment of the present invention.

Referring to FIG. 5, a test procedure method 100 is illustrated for testing the electrical connection of the pin 20 to circuitry 18 on circuit board 12. Method 100 includes step 102 of applying thermal energy (heat) to one or more pins or substrate area generally near the pin but outside the pin to circuit interface. Next, in step 104, method 100 waits a specified time for heat transfer to occur from the pin to the circuitry on the substrate. In step 106, method 100 acquires with the infrared camera the thermal image data near the interface, such as within a distance of about two millimeters from the interface. The data is analyzed with the computer system using a database of acceptable and unacceptable data in step 108. In decision step 110, method 100 determines whether the thermal image data meets certain requirements. If the requirements are met, the method 100 determines that the electrical connection is determined to be sufficient, and the test method 100 provides a passed output in step 114. If the thermal energy data does not meet the requirements, method 100 determines that the electrical conductivity and mechanical connection at the interface is not sufficient, and the test provides a failed output in step 112.

Figure 6:
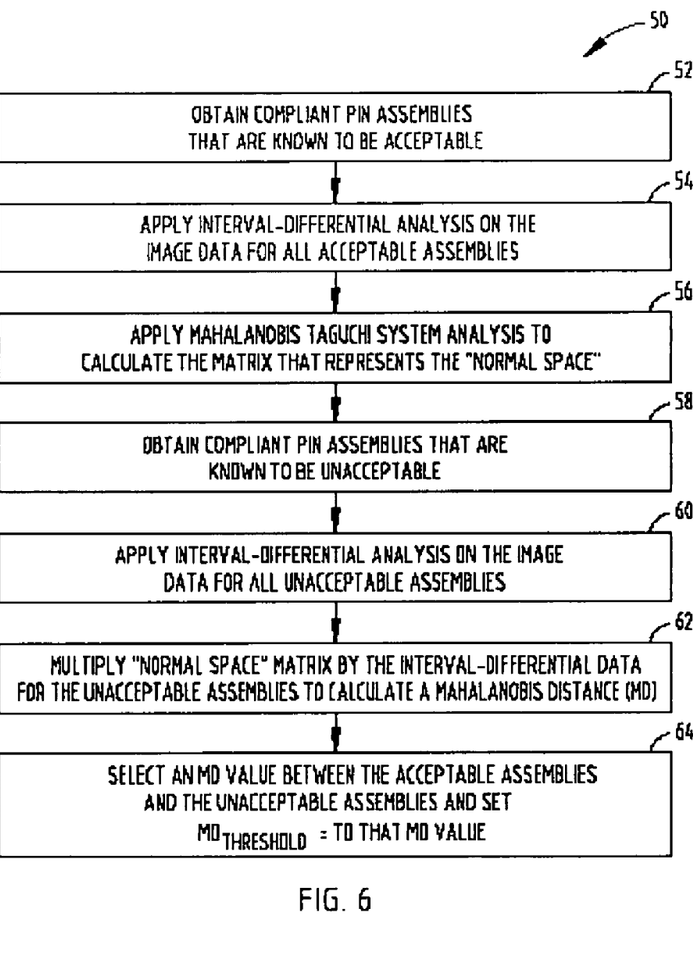
FIG. 6 is a flow diagram illustrating a training routine for establishing a threshold value for determining acceptable and unacceptable assemblies, according to one embodiment.

Referring to FIG. 6, the training routine 50 stored in memory 40 and executed by microprocessor 38 of computer system 36 is illustrated, according to one embodiment. The training routine 50 is executed as a pre-production training algorithm to establish a threshold value that distinguishes an acceptable electrical connection of an electronic assembly from an unacceptable connection of an electronic assembly. The training routine 50 begins with step 52 of obtaining compliant pin assemblies that are known to be acceptable. Training method 50 applies an interval-differential analysis on the image data for all acceptable assemblies, in step 54.

The interval-differential analysis is a well-known analysis procedure for analyzing the contour plot of temperature as a function of X and Y coordinates. The interval-differential analysis may include establishing temperature transitions and measuring distance to the various temperature transitions which are recorded as intervals. The distance transitions to the various temperature transitions from the contour plot are recorded and used as parameters in a Mahalanobis-Taguchi analysis.

The training method 50 then applies a Mahalanobis-Taguchi system analysis to calculate a matrix that represents the normal space. The Mahalanobis-Taguchi system is a well-known methodology for pattern recognition and is useful for discrimination between normal and abnormal samples. The calculated matrix that represents the normal space may include quantitative values of thermal intensity for a plurality of pixels.

Once the matrix has been calculated, the training method 50 obtains compliant pin assemblies that are known to be unacceptable in step 58. Next, in step 60, training method 50 applies the interval-differential analysis on the image data for all unacceptable assemblies. In step 62, method 50 multiplies the normal space matrix by the interval-differential data for the unacceptable assemblies to calculate a Mahalanobis distance (MD). The Mahalanobis distance (MD) is a distance measure based on correlations between variables by which different patterns can be identified and analyzed. It is particularly useful for determine similarity of an unknown sample set to a known one. The Mahalanobis distance is a metric calculator for each sample to be inspected and is an indicator of normality or abnormality. Generally, the larger the value of the Mahalanobis distance, the greater the abnormality. Typically, a threshold is selected where values lower than the threshold are considered normal and values larger than the threshold are considered abnormal.

The Mahalanobis distance from a group of values with a mean $\mu=(\mu_1, \mu_2, \mu_3, \ldots, \mu_p)$ and covariance matrix $\Sigma$ for a multivariate vector $x=(x_1, x_2, x_3, \ldots, x_p)$ may be defined by the following equation as:

$$D_M(x) = \sqrt{(x-\mu)^T \Sigma^{-1} (x-\mu)}.$$

Mahalanobis distance can also be defined as dissimilarity measure between two random vectors $\vec{x}$ and $\vec{y}$ of the same distribution with the covariance matrix $\Sigma$:

$$d(\vec{x}, \vec{y}) = \sqrt{(\vec{x}-\vec{y})^T \Sigma^{-1} (\vec{x}-\vec{y})}.$$

Finally, in step 64, training method 50 selects a Mahalanobis distance (MD) value between the acceptable assemblies and the unacceptable assemblies and sets a threshold $MD_{THRESHOLD}$ equal to the MD value. Accordingly, training method 50 establishes the threshold $MD_{THRESHOLD}$ that is then useful for analyzing an electrical circuit connection to determine if sufficient electrical conductivity is present in a production assembly product.

Figure 7:
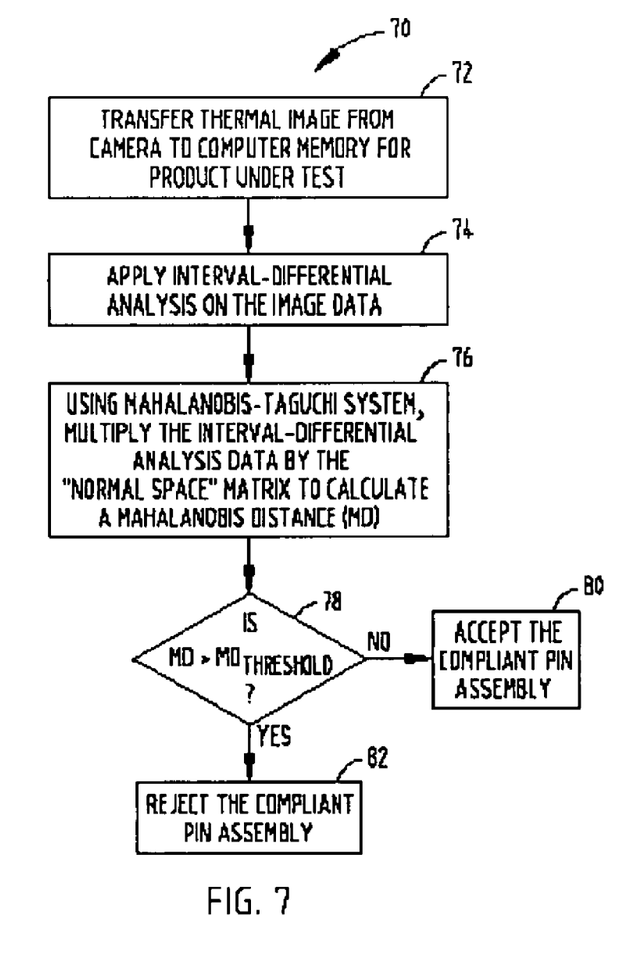
FIG. 7 is a flow diagram illustrating the test routine for determining acceptable and unacceptable electrical connections, according to one embodiment.

Referring to FIG. 7, the test routine 70 for testing the pin to circuit electrical connection, such as for an electronics product under test, is illustrated according to one embodiment. The test routine 70 begins at step 72 by transferring the thermal image from the infrared camera to the computer system memory for the current product under test. Next, in step 74, test routine 70 applies the interval-differential analysis on the acquired image data. In step 76, the test routine 70 uses the Mahalanobis-Taguchi system by multiplying the interval-differential analysis data by the normal space matrix to calculate a Mahalanobis distance (MD) value for the product under test.

Once the MD value for the product under test is established, the test routine 70 proceeds to decision step 78 to compare the MD value to the $MD_{THRESHOLD}$. If the MD value for the product under test is equal to or less than the $MD_{THRESHOLD}$, the test routine 70 determines that the compliant pin assembly is acceptable in step 80. If the MD value for the product under test is greater than the $MD_{THRESHOLD}$, the test routine 70 determines that the compliant pin assembly is unacceptable, and that the product should be rejected. The test routine 70 may be repeatedly used to test multiple products during or following production.

Figure 8:
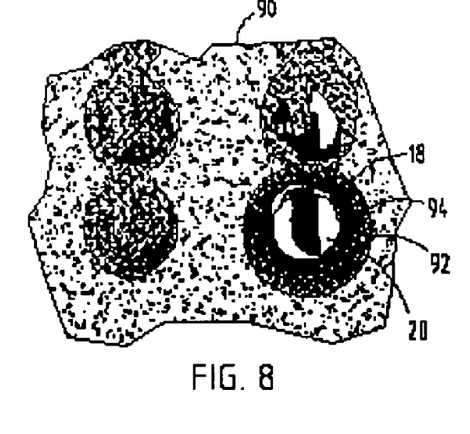
FIG. 8 is an image captured with the infrared camera showing sufficient electrical and mechanical connection of pin to circuit connections, according to one example.
Figure 9:
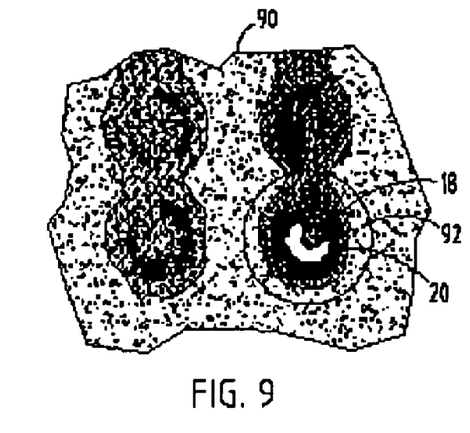
FIG. 9 is an image captured with the infrared camera illustrating a defective electrical and mechanical connection, according to one example.

Referring to FIGS. 8 and 9, examples of infrared images 90 captured with the infrared camera from an electronics device for both a good electrical connection and a poor electrical connection are illustrated when heat is applied to one end of the pin 20. In FIG. 8, a generally good electrical and mechanical connection is detected between the pin 20 and plated through hole circuit 18. The shaded region 94 within area 92 is generally shown having a higher thermal energy distribution, as compared to the same less region in area 92 in FIG. 9, which experiences a poor electrical and mechanical connection. When sufficient electrical connection is made between the pin 20 and circuit 18, the thermal energy distribution in the area 92 near the interface transfers heat from the interface to the surrounding area of the circuit board when the applied thermal energy is applied to the pin. When the applied thermal energy is applied to the circuit board, the thermal energy may transfer the heat energy from the circuit board to the pin by way of the interface, and the heat in the pin may be analyzed.

According to another embodiment, the method and test system may measure thermal energy radiation near the pin to circuit interface and analyze the measured thermal energy radiation to determine thermal energy distribution by monitoring rate of change of thermal energy. This may be achieved by analyzing periodic measurements of thermal energy radiation near the pin to circuit interface and determining the distribution of thermal energy as a function of how fast or how slow the thermal energy is conductively transferred through the pin to circuit interface. The sufficiency of the pin to circuit electrical and mechanical connection can then be based on the measured thermal energy distribution.

Accordingly, the test analysis method and system of the present invention advantageously provides for a technique of measuring electrical conductivity and mechanical connection between one or more pins 20 and circuitry 18 on the substrate 12. The test procedure is cost-effective, quick and easy to use, and generally does not impose special requirements on the configuration of the electrical circuitry in the product. While the test procedure has been illustrated in accordance with testing a single pin 20 on a plated through hole 18 of a circuit board 12, it should be appreciated that the procedure may be employed to test any of a number of electrical connections between one or more pins and circuitry on a substrate.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The invention claimed is:

1. A method of determining quality of an electrical connection of a pin connected to a circuit at an interface on a substrate of an electrical assembly, said method comprising the steps of:
    applying thermal energy to at least one of the pin and the substrate at a location outside of the pin to circuit interface;
    measuring thermal energy radiation near the pin to circuit interface;
    analyzing the measured thermal energy radiation to determine thermal energy distribution near the pin to circuit interface resulting from thermal conductivity at the interface; and
    determining quality of the pin to circuit electrical connection based on the determined thermal energy distribution;
    wherein the pin comprises a compliant pin press-fit into a plated through hole in the substrate.

2. The method as defined in claim 1, wherein the step of measuring thermal energy radiation comprises measuring infrared radiation.

3. The method as defined in claim 1, wherein the step of applying thermal energy comprising applying infrared energy.

4. The method as defined in claim 1, wherein the step of analyzing the measured thermal energy radiation comprises comparing the thermal energy distribution to known distributions for acceptable and unacceptable electrical assemblies.

5. The method as defined in claim 1, wherein the step of applying thermal energy comprises applying thermal energy to the pin.

6. The method as defined in claim 1, wherein the step of applying thermal energy comprises applying thermal energy to the substrate.

7. The method as defined in claim 1, wherein the step of applying thermal energy comprises applying electrical current to the pin.

8. The method as defined in claim 1, wherein the step of measuring thermal energy radiation near the pin to circuit interface comprises measuring thermal energy radiation within two millimeters of the interface.

9. The method as defined in claim 1, wherein the step of analyzing the measured thermal energy radiation to determine thermal energy distribution comprises analyzing rate of change of thermal energy near the pin to circuit interface.

10. A method of determining quality of an electrical connection of a compliant press-fit pin inserted into a conductive receptacle at an interface on a substrate of an electrical assembly, said method comprising the steps of:
    applying thermal energy to at least one of the compliant press-fit pin and the substrate at a location outside of the pin to receptacle interface;
    measuring thermal energy radiation near the pin to receptacle interface;
    analyzing the measured thermal energy radiation to determine thermal energy distribution near the pin to receptacle interface resulting from thermal conductivity at the interface; and
    determining quality of the pin to receptacle electrical connection based on the determined thermal energy distribution.

11. The method as defined in claim 10, wherein the step of measuring thermal energy radiation comprises measuring infrared radiation.

12. The method as defined in claim 10, wherein the step of applying thermal energy comprising applying infrared energy.

13. The method as defined in claim 10, wherein the receptacle comprises a plated through hole in the substrate.

14. The method as defined in claim 10, wherein the step of analyzing the measured thermal energy radiation comprises comparing the thermal energy distribution to known distributions for acceptable and unacceptable electrical assemblies.

15. The method as defined in claim 10, wherein the step of applying thermal energy comprises applying thermal energy to the pin.

16. The method as defined in claim 10, wherein the step of applying thermal energy comprises applying thermal energy to the substrate.

17. The method as defined in claim 10, wherein the step of applying thermal energy comprises applying electrical current to the pin.

18. The method as defined in claim 10, wherein the step of measuring thermal energy radiation near the pin to circuit interface comprises measuring thermal energy radiation within two millimeters of the interface.

19. The method as defined in claim 10, wherein the step of analyzing the measured thermal energy radiation to determine thermal energy distribution comprises analyzing rate of change of thermal energy near the pin to circuit interface.

20. A test system for determining quality of an electrical connection between a pin and a circuit at an interface on a substrate, said test system comprising:
   a heat source for applying thermal energy to one of a pin and a substrate at a location outside of the pin to circuit interface;
   a thermal energy measuring device for measuring thermal energy radiation near the pin to circuit interface; and
   a processor for analyzing the measured thermal energy radiation to determine thermal energy distribution near the pin to circuit interface resulting from thermal conductivity at the interface, said processor further determining quality of the pin to circuit electrical connection based on the determined thermal energy distribution;
   wherein the test system determines quality of a compliant press-fit pin inserted into a plated through hole on the substrate.

21. The test system as defined in claim 20, wherein the thermal energy measuring device comprises an infrared camera.

22. The test system as defined in claim 20, wherein the thermal energy source applies thermal energy radiation to the pin.

23. The test system as defined in claim 20, wherein the thermal energy source applies thermal energy radiation to the substrate.

24. The test system as defined in claim 20, wherein the thermal energy measuring device measures thermal radiation within about two millimeters of the interface.

25. The test system as defined in claim 20, wherein the processor analyzes rate of change of thermal energy to determine the thermal energy distribution.

* * * * *